United States Patent
Gallitano-Mendel

(10) Patent No.: US 11,147,888 B2
(45) Date of Patent: Oct. 19, 2021

(54) METHODS AND SYSTEMS FOR DETECTING PSYCHOTIC DISORDERS ASSOCIATED WITH SEROTONIN 2A RECEPTOR DEFICIENCIES

(71) Applicant: ARIZONA BOARD OF REGENTS ON BEHALF OF THE UNIVERSITY OF ARIZONA, Tucson, AZ (US)

(72) Inventor: Amelia L. Gallitano-Mendel, Phoenix, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 106 days.

(21) Appl. No.: 16/067,735

(22) PCT Filed: Jan. 6, 2017

(86) PCT No.: PCT/US2017/012571
§ 371 (c)(1),
(2) Date: Jul. 2, 2018

(87) PCT Pub. No.: WO2017/120494
PCT Pub. Date: Jul. 13, 2017

(65) Prior Publication Data
US 2019/0000999 A1 Jan. 3, 2019

Related U.S. Application Data

(60) Provisional application No. 62/276,040, filed on Jan. 7, 2016.

(51) Int. Cl.
*A61K 49/00* (2006.01)
*A61K 31/5513* (2006.01)
*A61P 25/18* (2006.01)

(52) U.S. Cl.
CPC ...... *A61K 49/0004* (2013.01); *A61K 31/5513* (2013.01); *A61K 49/00* (2013.01); *A61P 25/18* (2018.01)

(58) Field of Classification Search
None
See application file for complete search history.

(56) References Cited

U.S. PATENT DOCUMENTS

2005/0148018 A1 7/2005 Weiner et al.

OTHER PUBLICATIONS

Williams et al., Reduced Levels of Serotonin 2A Receptors Underlie Resistance of Egr3-Deficient Mice to Locomotor Suppression by Clozapine, Neuropsychopharmacology, vol. 37, 2012.pp. 2285-2298.
Gallitano-Mendel et al., Mice Lacking the Immediate Early Gene Egr3 Respond to the Anti-Aggressive Effects of Clozapine Vet are Relatively Resistant to its Sedating Effects, Public Access, Author Manuscript, PMC Oct. 27, 2015.
Mcomish et al. Clozapine-Induced Locomotor Suppression is Mediated by 5-HT2A Receptors in the Forebrain. Neuropsychopharmacology (2012) 37, 2747-2755.
Gronli et al. Sleep Homeostatic and Waking Behavioral Phenotypes in Egr3-Deficient Mice Associated with Serotonin Receptor 5-HT2 Deficits. SLEEP, vol. 39, No. 12, 2016.
Cutler, Pharmacokinetic Studies of Antipsychotics in Healthy Volunteers Versus Patients, J Clin Psychiatry 2001;62 (suppl 5).

*Primary Examiner* — Jennifer Lamberski
(74) *Attorney, Agent, or Firm* — Nguyen Tarbet LLC

(57) ABSTRACT

Methods for detecting resistance to sedation caused by antipsychotic drugs including methods for detecting psychotic disorders such as but not limited to schizophrenia or bipolar I disorder featuring administering to a patient a dose of an antipsychotic medication; and subjecting the patient to an evaluation at a time point following administration of the dose of the antipsychotic medication. The evaluation is adapted to determine a level of sedation resulting from the dose of the antipsychotic medication. A resulting level of sedation may be one of the following: completely sedated, significantly sedated, moderately sedated, not significantly sedated and completely alert. If the individual is not completely sedated or significantly sedated, or is completely alert, then the patient may have a likelihood of having a psychotic disorder such as schizophrenia.

12 Claims, 5 Drawing Sheets

FIG. 4A
FIG. 4B
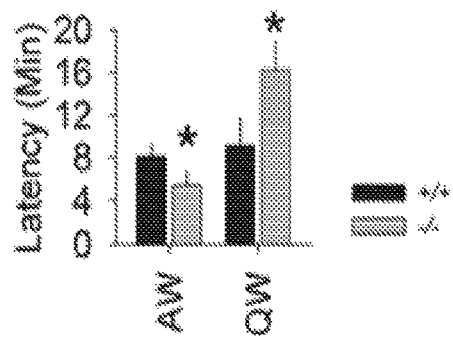
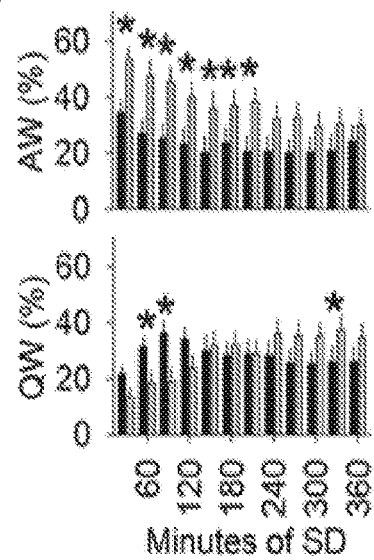
FIG. 4C
FIG. 4D
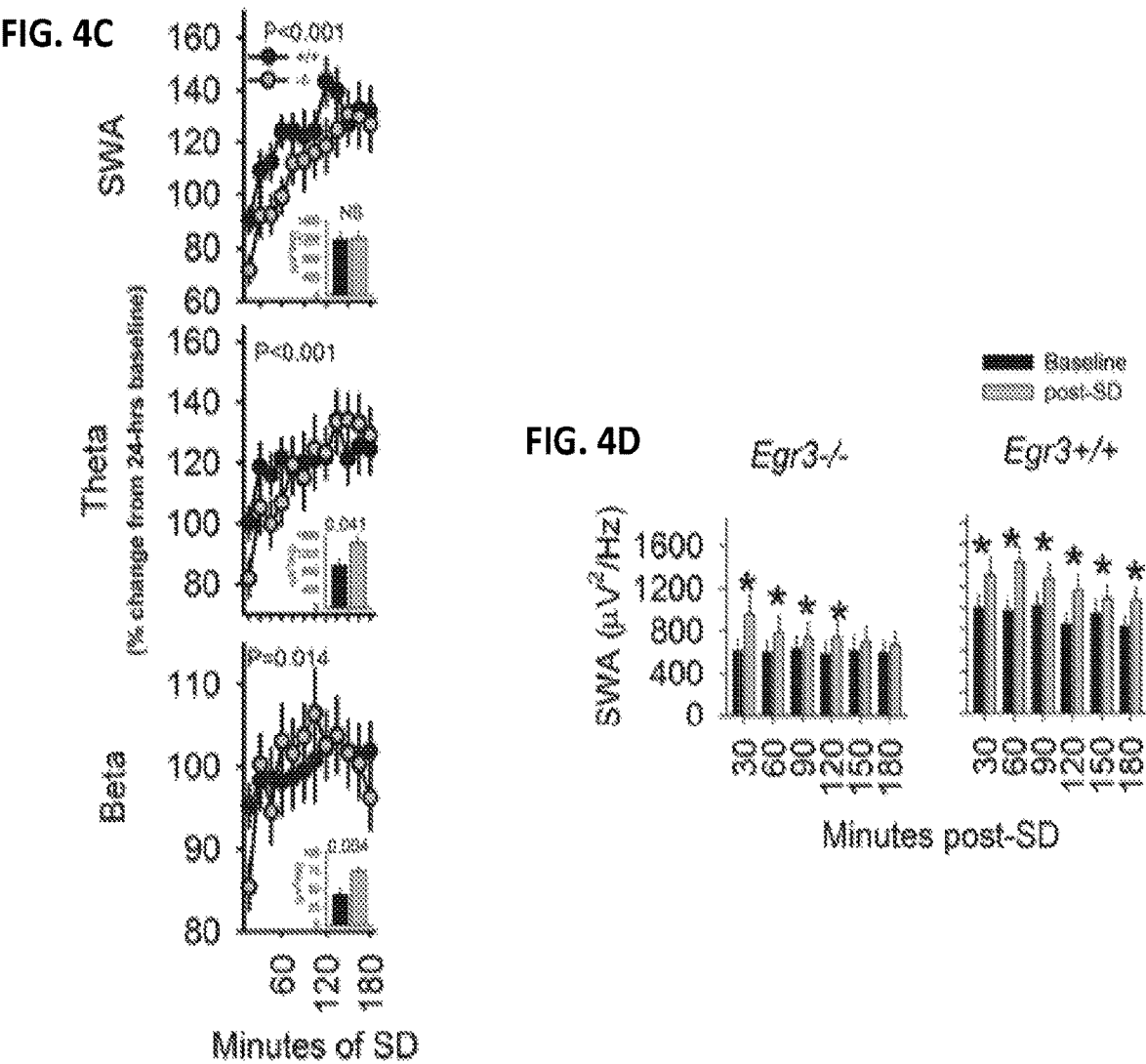

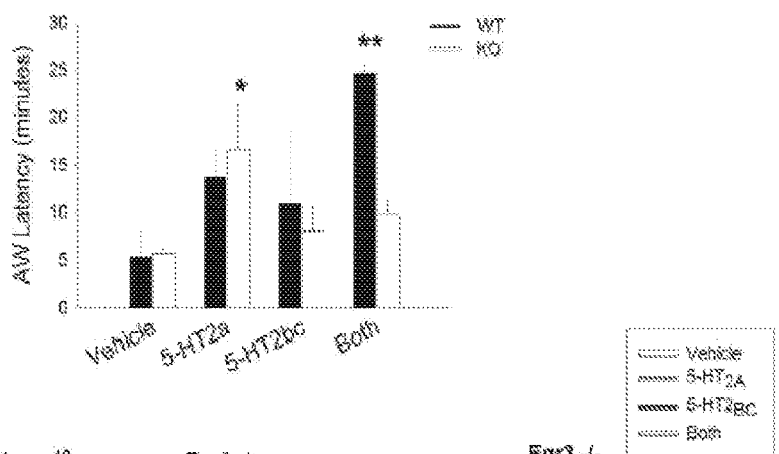
FIG. 6A
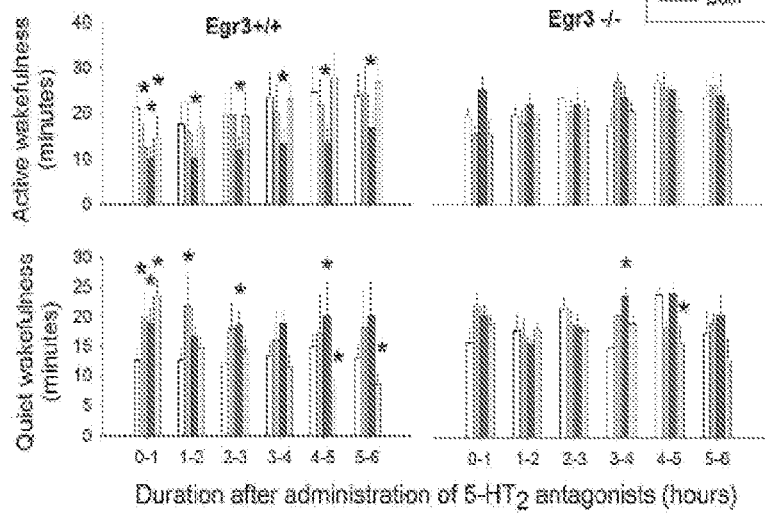
FIG. 6B
FIG. 6C
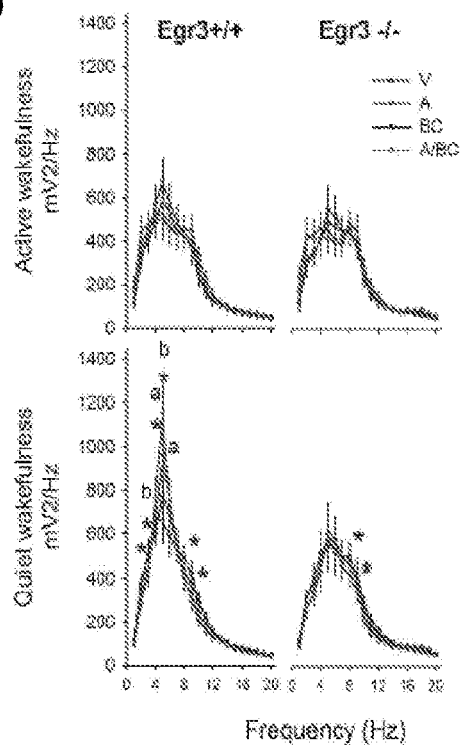
FIG. 6D

METHODS AND SYSTEMS FOR DETECTING PSYCHOTIC DISORDERS ASSOCIATED WITH SEROTONIN 2A RECEPTOR DEFICIENCIES

CROSS REFERENCE

This application claims priority to U.S. Provisional Patent Application No. 62/276,040, filed Jan. 7, 2016, the specification(s) of which is/are incorporated herein in their entirety by reference.

GOVERNMENT SUPPORT

This invention was made with government support under Grant No. R01 MH097803, awarded by NIH. The government has certain rights in the invention.

FIELD OF THE INVENTION

The present invention relates to methods of detecting psychotic illnesses, e.g., psychotic illnesses associated with deficiencies in serotonin 2A receptors/receptor activity (and/or increases in serotonin 1A receptors/receptor activity), more particularly to methods of detecting resistance to sedation normally caused by certain drugs (e.g., certain antipsychotic drugs) which may be indicative of a psychotic illness associated with deficiencies in serotonin 2A receptors/receptor activity (and/or increases in serotonin 1A receptors/receptor activity), e.g., diagnosing or detecting schizophrenia or diagnosing a patient with a high probability of having schizophrenia or a particular subtype of schizophrenia or distinguishing schizophrenia from other causes of psychosis, or diagnosing other psychotic disorders such as but not limited to bipolar disorder (e.g., bipolar I disorder, etc.).

BACKGROUND OF THE INVENTION

Schizophrenia is a severe psychotic illness of unknown cause that affects 1% of the population worldwide. Currently, there is no diagnostic test for schizophrenia. Instead, the diagnosis is typically established through a psychiatric interview of the patient, who is evaluated against a set of established criteria of signs and symptoms. It can take many months to years to establish a diagnosis of schizophrenia and achieve an appropriate treatment regimen to attain resolution of the patient's symptoms. This process is particularly challenging in areas of limited access to specialists, a problem not only in third world countries and rural regions, but throughout the United States where there can be long waits to obtain an appointment with a psychiatrist.

The present invention features methods for detecting or diagnosing schizophrenia and methods of distinguishing schizophrenia from other causes of psychosis. The present invention also features detecting or diagnosing a psychotic disorder (such as but not limited to Bipolar I disorder), e.g., a psychotic disorder associated with deficiencies in serotonin 2A receptors/receptor activity (and/or increases in serotonin 1A receptors/receptor activity). The present invention also features distinguishing a psychotic disorder (such as but not limited to Bipolar I disorder) from other causes of psychosis. The present invention also features detecting resistance to sedative effects of particular drugs such as antipsychotic drugs. In some embodiments, the method comprises administering a dose of an antipsychotic medication or a medication that binds to serotonin 2A receptors (or other appropriate medication) to an individual suspected of having schizophrenia (or other psychotic disorder, e.g., Bipolar I, etc.) and subjecting the individual to an evaluation adapted to determine the degree of sleepiness or sedation in response to the dose of the antipsychotic medication. The evaluation may comprise one or more of the following: a physical examination, a questionnaire, or any other appropriate approach to evaluating sleepiness or sedation. A high resistance to the sedative/sleepiness side effects that are typically caused by the antipsychotic medication may be considered indicative of a psychotic disorder, e.g., schizophrenia, bipolar I, etc., or indicative of a high probability of a psychotic disorder, e.g., schizophrenia, bipolar I, etc. Note that deficiencies in receptor activity (e.g., serotonin 2A receptor) may be caused by various states, e.g., a reduction in the number of receptors, dysfunctional receptors, etc. Increases in receptor activity (e.g., serotonin 1A receptor) may be caused by various states, e.g., an increase in the number of receptors, hyperactive receptors, etc.

In some embodiments, the method comprises evaluating a biological sample (e.g., blood or other appropriate biological sample) of the individual. For example, in some embodiments, the method comprises assessing peripheral levels of the serotonin 2A receptor. In some embodiments, the method comprises assessing levels of serotonin 1A receptor The results of the biological sample evaluation may be correlated with a diagnosis of a psychotic disorder, e.g., schizophrenia, bipolar I, etc., as appropriate.

Without wishing to limit the present invention to any theory or mechanism, it is believed that the methods of the present invention may help ascertain with a high degree of assuredness whether or not the individual has a psychotic disorder, e.g., schizophrenia, bipolar I, etc. In some embodiments, the methods of the present invention may be used to help ascertain whether or not the individual has a specific subtype of a psychotic disorder, e.g., subtype of schizophrenia (e.g., one characterized by decreased levels of brain serotonin 2A receptors).

The methods of the present invention may provide benefits, for example the methods may help (a) decrease the time to diagnosis, (b) identify a subtype of schizophrenia (schizophrenia is currently a broad diagnosis widely believed to encompass numerous biologically distinct illnesses), which may allow for the development of personalized treatments, (c) distinguish schizophrenia from other causes of psychosis; (d) provide a diagnostic tool that can be performed by a non-physician in areas with limited access to health care or specialists, and/or (e) improve research by helping to clarify diagnostic groups and provide a biological marker of the illness.

SUMMARY OF THE INVENTION

The present invention features methods for detecting or diagnosing psychotic disorders, e.g., psychotic disorders associated with deficiencies in serotonin 2A receptors/receptor activity (and/or increases in serotonin 1A receptors/receptor activity), e.g., schizophrenia, bipolar I disorder, etc. The present invention also features methods of distinguishing psychotic disorders, e.g., psychotic disorders associated with deficiencies in serotonin 2A receptors/receptor activity (and/or increases in serotonin 1A receptors/receptor activity) such as but not limited to schizophrenia, bipolar I disorder, etc., from other causes of psychosis. The present invention also features detecting resistance to sedative effects of particular drugs such as antipsychotic drugs.

Without wishing to limit the present invention to any theory or mechanism, the present invention may allow for distinguishing certain psychotic disorders (e.g., psychotic disorders associated with deficiencies in serotonin 2A receptors/receptor activity and/or increases in serotonin 1A receptors/receptor activity, e.g., schizophrenia, bipolar I disorder, etc.) from other causes of psychosis, e.g., psychiatric illnesses (such as but not limited to bipolar disorder I, major depression with psychotic features, delusional disorder, PTSD), medical illnesses (such as but not limited to delirium, toxicity of a drug, imbalance of electrolytes, hormones, other metabolic disturbances, infection, etc.), effects of drugs or alcohol, etc.

In some embodiments, the method comprises administering to the patient a dose of an antipsychotic medication (e.g., clozapine, a derivative of clozapine, a second-generation antipsychotic, a selective 5-HT2AR antagonist, or a derivative of a selective 5-HT2AR antagonist, a 5-HT2AR inverse agonist, or a derivative of a 5-HT2AR inverse agonist) or a medication that binds to serotonin 2A receptors (or other appropriate medication); and subjecting the patient to an evaluation at a time point following administration of the dose of the antipsychotic medication. The evaluation may be adapted to determine a level of sedation resulting from the dose of the antipsychotic medication. In some embodiments, the level of sedation is within a range from a high of level sedation to zero level sedation. In some embodiments, the more the individual experiences sedation toward the high level of sedation then the less probability the individual has a particular psychotic disorder such as one associated with deficiencies in serotonin 2A receptors (and/or elevations in serotonin 1A receptors), e.g., schizophrenia, bipolar I disorder, etc. In some embodiments, the more the individual experiences sedation toward the zero level of sedation then the more the probability that the individual has a particular psychotic disorder such as one associated with deficiencies in serotonin 2A receptors(and/or elevations in serotonin 1A receptors), e.g., schizophrenia, bipolar I disorder, etc.

In some embodiments, the level of sedation may include completely sedated, significantly sedated, moderately sedated, not significantly sedated and completely alert. In some embodiments, if the individual is not completely sedated or significantly sedated, the patient has a likelihood of having a particular psychotic disorder such as one associated with deficiencies in serotonin 2A receptors, e.g., schizophrenia, bipolar I disorder, etc.

In some embodiments, the time point following administration of the medication is 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes 170 minutes, 180 minutes, from 5 to 10 minutes, from 10 to 30 minutes, from 15 to 60 minutes, from 5 to 120 minutes, from 10 to 180 minutes, or more than 180 minutes, e.g., 210 minutes, 240 minutes, 300 minutes, etc.

In some embodiments, the dose of the antipsychotic medication is effective for rendering an individual who does not have schizophrenia completely sedated or significantly sedated at the time point following administration of the antipsychotic medication.

In some embodiments, the evaluation comprises measurement of one or more of the following parameters: pulse, oxygen saturation, blood pressure, and respiratory rate. In some embodiments, the evaluation comprises subjecting the patient to a stimulus and measuring the result of the stimulus. In some embodiments, the stimulus comprises a sternal rub, nail bed pressure, or smelling salts. In some embodiments, if the individual is not aroused by a sternal rub, nail bed pressure, or smelling salts then he/she is completely sedated.

In some embodiments, the evaluation comprises administering a questionnaire to the patient. In some embodiments, the evaluation comprises determining whether the individual can keep his/her eyes open for a time period (e.g., 5 seconds, 10 seconds, 15 seconds, or 20 seconds, etc.). In some embodiments, the evaluation comprises using the Stanford Sleepiness Scale (SSS) or the psychomotor vigilance task (PVT), Epworth Sleepiness Scale (ESS), Chalder Fatigue Scale (CFM), and/or Fatigue Severity Scale (FSS), and/or the Pasero Opioid-Induced Sedation Scale (FOSS).

The present invention features a method for detecting a deficiency in serotonin 2A receptor activity or elevations in serotonin 1A receptor in a patient displaying signs or symptoms of a psychotic disorder. The present invention also features a method for detecting a deficiency in serotonin 2A receptor activity in a patient displaying signs or symptoms of a psychotic disorder. In some embodiments, the method comprises administering to the patient a dose of an antipsychotic medication; and subjecting the patient to an evaluation at a time point following administration of the dose of the antipsychotic medication, the evaluation is for determining a level of sedation resulting from the dose of the antipsychotic medication, the level of sedation being in a range of high level of sedation to zero level of sedation. In some embodiments, if the sedation is toward the high level of sedation then the patient does not have a deficiency in serotonin 2A receptor activity, or does not have an elevation in serotonin 1A receptor activity, whereas if the sedation is toward the zero level of sedation then the patient does have a deficiency in serotonin 2A receptor activity or an elevation in serotonin 1A receptor activity.

The present invention also features a method of detecting schizophrenia in a patient displaying signs or symptoms of schizophrenia. In some embodiments, the method comprises administering to the patient a dose of an antipsychotic medication; and subjecting the patient to an evaluation at a time point following administration of the dose of the antipsychotic medication, the evaluation is for determining a level of sedation resulting from the dose of the antipsychotic medication, the level of sedation being in a range of high level of sedation to zero level of sedation. In some embodiments, if the level of sedation is toward the high level of sedation then the patient does not have schizophrenia, whereas if the level of sedation is toward the zero level of sedation then the individual has schizophrenia.

The present invention also features a method of treating schizophrenia, in some embodiments, the method comprises administering to a patient suspected of having schizophrenia a dose of an antipsychotic medication; and subjecting the patient to an evaluation at a time point following administration of the dose of the antipsychotic medication, the evaluation is for determining a level of sedation resulting from the dose of the antipsychotic medication, the level of sedation being in a range of high level of sedation to zero level of sedation (in some embodiments, if the level of sedation is toward the high level of sedation then schizophrenia is not detected in the patient, whereas if the level of sedation is toward the zero level of sedation then schizophrenia is detected in the patient); and administering an anti-schizophrenia medication to the patient, wherein the anti-schizophrenia medication is effective for reducing symptoms of schizophrenia.

The present invention also features a method of differentiating between a psychotic disorder associated with deficiencies in serotonin 2A receptor activity and a psychotic disorder not associated with deficiencies in serotonin 2A receptor activity. In some embodiments, the method comprises administering to a patient a dose of an antipsychotic medication; and subjecting the patient to an evaluation at a time point following administration of the dose of the antipsychotic medication, the evaluation is for determining a level of sedation resulting from the dose of the antipsychotic medication, the level of sedation being in a range of high level of sedation to zero level of sedation. In some embodiments, if the sedation is toward the high level of sedation then the patient does not have a psychotic disorder associated with a deficiency in serotonin 2A receptor activity, whereas if the sedation is toward the zero level of sedation then the patient does have a psychotic disorder associated with a deficiency in serotonin 2A receptor activity.

In some embodiments, the antipsychotic medication comprises clozapine, a derivative of clozapine, a second-generation antipsychotic, a selective 5-HT2AR antagonist, a derivative of a selective 5-HT2AR antagonist, a 5-HT2AR inverse agonist, a derivative of a 5-HT2AR inverse agonist, or a combination thereof. In some embodiments, the time point following administration of the medication is 10 minutes, 20 minutes, 30 minutes, 40 minutes, 50 minutes, or 60 minutes, 70 minutes, 80 minutes, 90 minutes, 100 minutes, 110 minutes, 120 minutes, 130 minutes, 140 minutes, 150 minutes, 160 minutes 170 minutes, 180 minutes, from 5 to 10 minutes, from 10 to 30 minutes, from 15 to 60 minutes, from 5 to 120 minutes, from 10 to 180 minutes, or more than 180 minutes. In some embodiments, a deficiency in serotonin 2A receptor activity is associated with schizophrenia or bipolar I disorder. In some embodiments, the dose of the antipsychotic medication is effective for rendering a non-schizophrenic individual completely sedated or significantly sedated at the time point following administration of the antipsychotic medication. In some embodiments, the evaluation comprises measurement of one or more of the following parameters: pulse, oxygen saturation, blood pressure, and respiratory rate. In some embodiments, the evaluation comprises subjecting the patient to a stimulus and measuring the result of the stimulus (e.g., sternal rub, nail bed pressure, or smelling salts). In some embodiments, if the individual is not aroused by a sternal rub, nail bed pressure, or smelling salts then he/she has a high level of sedation. In some embodiments, the evaluation comprises administering a questionnaire to the patient. In some embodiments, the evaluation comprises determining whether the individual can keep his/her eyes open for a time period. In some embodiments, the time period is from 5 to 10 seconds, from 10 to 30 seconds, or from 10 to 60 seconds. In some embodiments, the evaluation comprises using Stanford Sleepiness Scale (SSS), Psychomotor Vigilance Task (PVT), Epworth Sleepiness Scale (ESS), Chalder Fatigue Scale (CFM), Fatigue Severity Scale (FSS), the Pasero Opioid-Induced Sedation Scale (FOSS), or a combination thereof. In some embodiments, the evaluation comprises using a Bispectral Index. In some embodiments, the Bispectral Index is a scale of sedation from 0 to 100, wherein 100 is awake and 0 is a flatline EEG.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 4A shows latency to 2 minutes accumulated active wakefulness (AW) and quiet wakefulness (QW) in response to 6 hrs sleep disruption.

FIG. 4B shows time spent in AW and QW during session of 6 hrs sleep disruption (SD).

FIG. 4C shows progressive increase in slow wave activity (SWA; 1-4 Hz), theta (5-8 Hz), and beta (15-35 Hz) activity during quiet wakefulness over the time course of 6 hrs sleep disruption. The insets show the absolute EEG power.

FIG. 4D shows sleep intensity (SWA) during recovery sleep and time matched baseline condition. Asterisks indicate significant differences between Egr3-deficient mice (n=15) and wild type mice (n=16). Data are shown as mean values +/− standard error of the mean. Squares indicate significant differences compared to baseline level. P values indicate main effect of time (repeated-measures analysis of variance). Sex differences were not detected.

FIG. 6A shows latency to 2 minutes accumulated active wakefulness (AW) after 5-HT2 antagonists treatment (5 mg/kg) in Egr3-deficient mice (n=7) and wild type mice (n=8).

FIG. 6B shows time spent in active wakefulness and quiet wakefulness after vehicle. Asterisks indicate significant differences compared to vehicle treatment.

FIG. 6C shows time spent in active wakefulness and quiet wakefulness after vehicle. Asterisks indicate significant differences compared to vehicle treatment.

FIG. 6D shows waking EEG spectral power. "a" and "b" and asterisks indicate significant differences compared to vehicle treatment, 5-HT2A, 5-HT2BC or both antagonist, respectively. Sex differences were not detected.

DETAILED DESCRIPTION OF THE INVENTION

Figure 1:
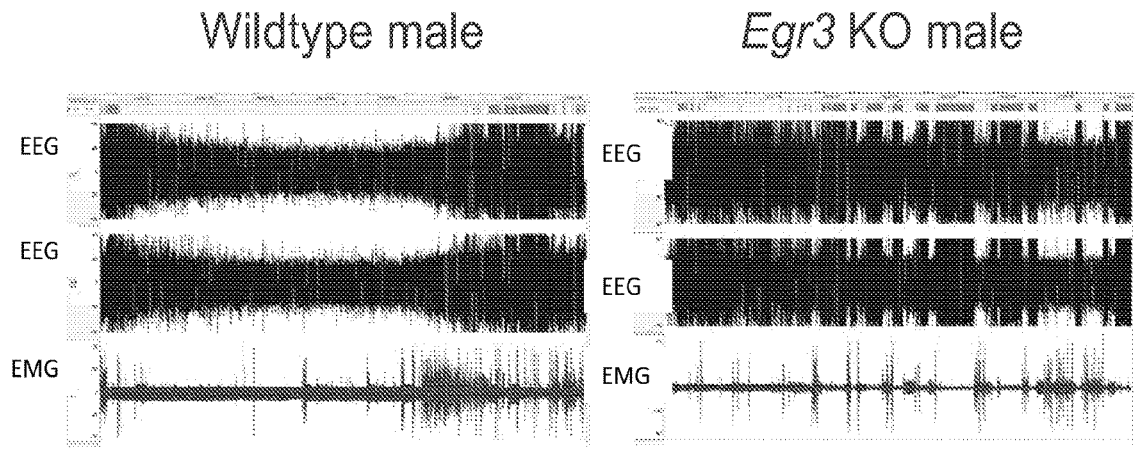
FIG. 1 shows EEG recordings of early growth response 3 knockout (Egr3KO, e.g., Egr3−/−) mice vs. wild type (WT) mice in response to clozapine (4 hour recording after high dose clozapine; EEG channels are upper two traces, EMG lower traces).
Figure 2A:
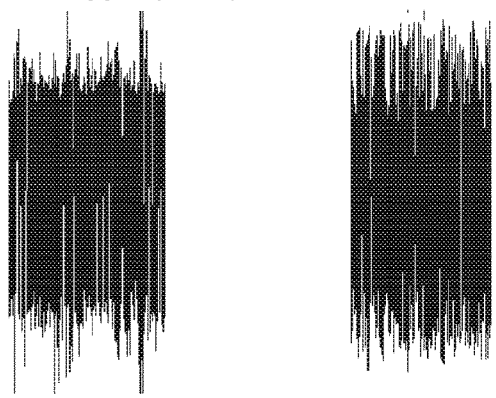
FIG. 2A shows representative sample EEG traces (20-min) from a wild type mouse (left) and an Egr3−/− mouse (right). Mice were spontaneously awake in undisturbed home cage conditions throughout the 20-minute interval. During dark phase.
Figure 2B:
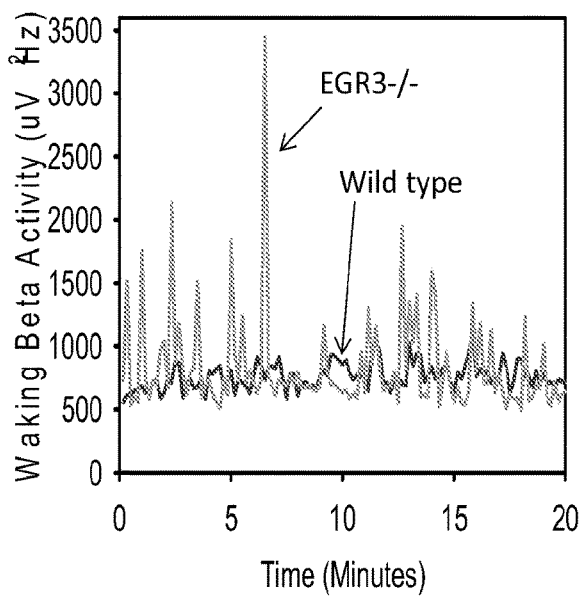
FIG. 2B shows EEG state instability in Egr3-deficient mice. EEG beta (15-35 Hz) activity measured by FFT (in 10 sec epochs) of 20-min EEG recordings from a wild type mouse (red) and an Egr3−/− mouse (orange).
Figure 2C:
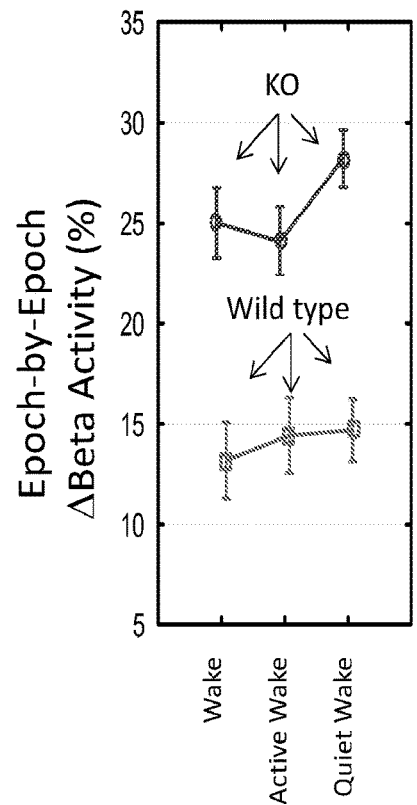
FIG. 2C shows averaged epoch-by-epoch change in beta activity across consecutive epochs of wake, and the active and quiet substates of wake, in wild type (red, n=12) and Egr3−/− (blue, n=13) mice. Values are normalized as a percent of absolute beta activity.
Figure 3A:
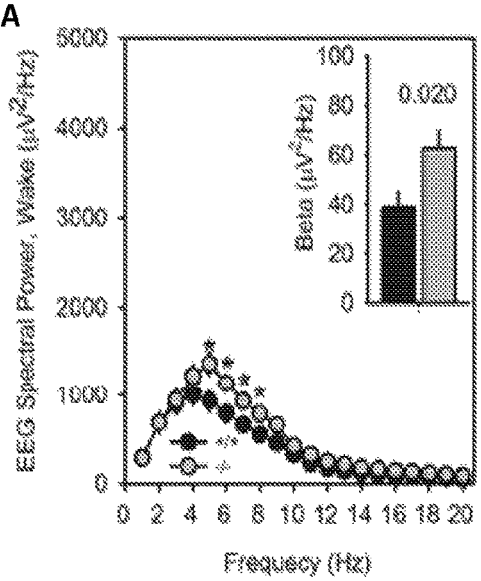
FIG. 3A shows the effect of Egr3 disruption on the electroencephalographic (EEG) power profiles of the wake state. Mean values +/− standard error of the mean in the 1 to 20 Hz and beta (15-35 Hz) range across the 24 h baseline recording are shown. Asterisks indicate significant differences between Egr3-deficient mice (n=15) and wild type mice (n=16). Sex differences were not detected.
Figure 3B:
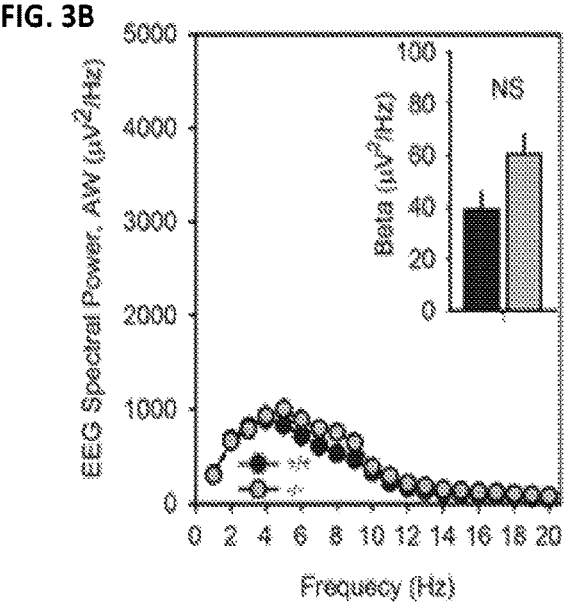
FIG. 3B shows the effect of Egr3 disruption on the electroencephalographic (EEG) power profiles of the active wakefulness (AW) state. Mean values +/− standard error of the mean in the 1 to 20 Hz and beta (15-35 Hz) range across the 24 h baseline recording are shown. Asterisks indicate significant differences between Egr3-deficient mice (n=15) and wild type mice (n=16). Sex differences were not detected.
Figure 3C:
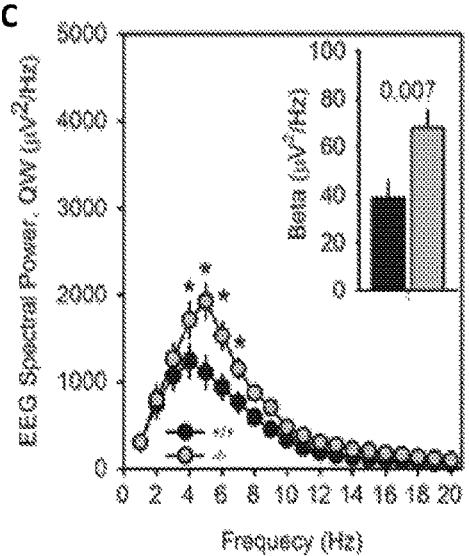
FIG. 3C shows the effect of Egr3 disruption on the electroencephalographic (EEG) power profiles of the quiet wakefulness (QW) state. Mean values +/− standard error of the mean in the 1 to 20 Hz and beta (15-35 Hz) range across the 24 h baseline recording are shown. Asterisks indicate significant differences between Egr3-deficient mice (n=15) and wild type mice (n=16). Sex differences were not detected.
Figure 3D:
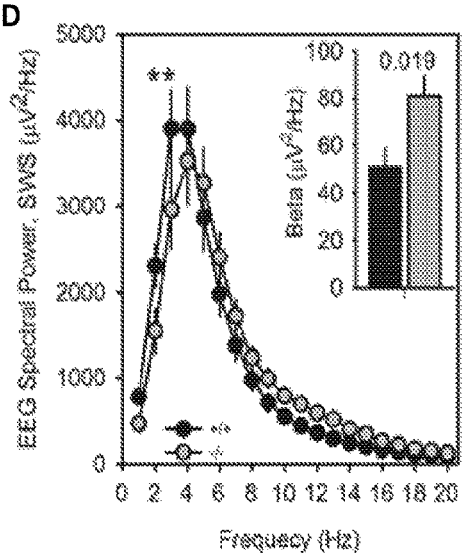
FIG. 3D shows the effect of Egr3 disruption on the electroencephalographic (EEG) power profiles of the slow wave sleep (SWS) state. Mean values +/− standard error of the mean in the 1 to 20 Hz and beta (15-35 Hz) range across the 24 h baseline recording are shown. Asterisks indicate significant differences between Egr3-deficient mice (n=15) and wild type mice (n=16). Sex differences were not detected.
Figure 3E:
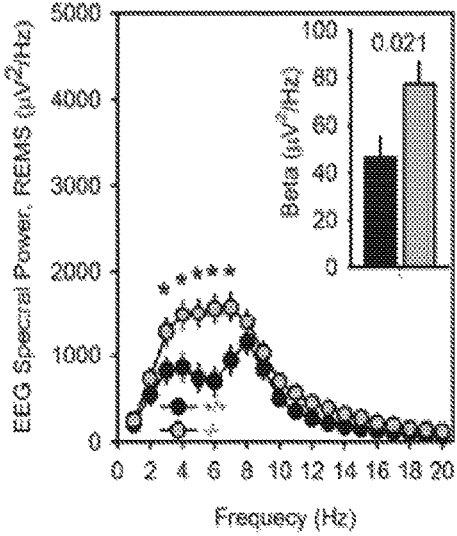
FIG. 3E shows the effect of Egr3 disruption on the electroencephalographic (EEG) power profiles of the rapid eye movement sleep (REMS) state. Mean values +/− standard error of the mean in the 1 to 20 Hz and beta (15-35 Hz) range across the 24 h baseline recording are shown. Asterisks indicate significant differences between Egr3-deficient mice (n=15) and wild type mice (n=16). Sex differences were not detected.

The present invention features methods for detecting or diagnosing psychotic disorders, e.g., psychotic disorders associated with deficiencies in serotonin 2A receptors/receptor activity (and/or increases in serotonin 1A receptors/receptor activity), e.g., schizophrenia, bipolar I disorder, etc. The present invention also features methods of distinguishing psychotic disorders, e.g., psychotic disorders associated with deficiencies in serotonin 2A receptors/receptor activity (and/or increases in serotonin 1A receptors/receptor activity) such as but not limited to schizophrenia, bipolar I disorder, etc., from other causes of psychosis. The present invention also features detecting resistance to sedative effects of particular drugs such as antipsychotic drugs.

As previously discussed, the methods may comprise administering a dose of an antipsychotic medication to an individual displaying signs or symptoms of a psychotic disorder associated with a deficiency in serotonin 2A receptors/receptor activity and/or increases in serotonin 1A receptors/receptor activity (e.g., schizophrenia, bipolar I disorder, etc.) and subjecting the individual to an evaluation adapted to determine the degree of sleepiness or sedation resulting from the dose of the antipsychotic medication. Without wishing to limit the present invention to any theory or mechanism, it is believed that the degree of sleepiness or sedation resulting from the dose of the antipsychotic medication may be able to be correlated with the presence of the psychotic disorder associated with a deficiency in serotonin 2A receptors/receptor activity and/or increases in serotonin 1A receptors/receptor activity (e.g., schizophrenia, bipolar I disorder, etc.). For example, a high resistance to the sedative/sleepiness side effects that are typically caused by the antipsychotic medication (e.g., lack of sedation) may be considered indicative of schizophrenia or indicative of a high probability of schizophrenia. Or, in some embodiments, a low resistance to the sedative/sleepiness side effects that are typically caused by the antipsychotic medication (e.g., complete sedation) may be considered indicative that the individual does not have schizophrenia (or bipolar I, etc.) or indicative of a high probability that the individual does not have schizophrenia (or bipolar I, etc.).

In some embodiments, the antipsychotic medication comprises: clozapine, an appropriate derivative of clozapine, a second-generation antipsychotic, a selective 5-HT2AR antagonist (e.g., M100907 (Volinanserin)), an appropriate derivative of the selective 5-HT2AR antagonist, a 5-HT2AR inverse agonist (e.g., pimavanserin (APC-103), a derivative thereof, ziprasidone, olanzapine, or the like. The present invention is not limited to the aforementioned medications.

In some embodiments, the evaluation comprises a physical examination (or a physical stimulation). In some embodiments, the evaluation comprises a questionnaire. The present invention is not limited to the aforementioned types of evaluations and may include any other appropriate types of evaluations or combinations of types of evaluations. A physical examination may include measuring pulse, respiratory rate, blood pressure, oxygen saturation, the like, or a combination thereof. In some embodiments, the physical examination comprises subjecting the patient to a stimulus and measuring the response to the stimulus, e.g., to determine arousability, responsiveness, alertness, etc. For example, in some embodiments, the patient is subjected to a sternal rub. In some embodiments, the patient is subjected to nail bed pressure. In some embodiments, the patient is subjected to smelling salts. In some embodiments, failure to arouse after a sternal rub is indicative of complete sedation (or significant sedation, etc.). In some embodiments, failure to arouse after nail bed pressure is indicative of complete sedation (or significant sedation, etc.). In some embodiments, failure to arouse after smelling salts is indicative of complete sedation (or significant sedation, etc.).

In some embodiments, the examination comprises asking the patient to open his/her eyes for a period of time (e.g., 5 seconds, 10 seconds, 15 seconds, 20 seconds, 25 seconds, 30 seconds, 35 seconds, 40 seconds, 45 seconds, 50 seconds, 55 seconds, 60 seconds, more than 60 seconds, 0 to 5 seconds, 5 to 10 seconds, 5 to 15 seconds, 10 to 30 seconds, 10 to 60 seconds, the like, etc.). In some embodiments, failure to keep the eyes open for that period of time is indicative of complete sedation (or significant sedation, etc.).

In some embodiments, complete sedation (or significant sedation) is indicative of a lack of schizophrenia or indicative of a high probability of lack of the psychotic disorder associated with a deficiency in serotonin 2A receptors/receptor activity and/or increases in serotonin 1A receptors/receptor activity (e.g., schizophrenia, bipolar I disorder, etc.). In some embodiments, lack of complete sedation or lack of significant sedation (e.g., resistance to sedative effects of the medication) is indicative of the psychotic disorder associated with a deficiency in serotonin 2A receptors/receptor activity and/or increases in serotonin 1A receptors/receptor activity (e.g., schizophrenia, bipolar I disorder, etc.) or indicative of a high probability of the psychotic disorder associated with a deficiency in serotonin 2A receptors/receptor activity and/or increases in serotonin 1A receptors/receptor activity (e.g., schizophrenia, bipolar I disorder, etc.).

In some embodiments, the patient is evaluated using a questionnaire. In some embodiments, the questions are used to help determine sleepiness or sedation levels. In some embodiments, the time needed for the patient to respond to various questions is used to help determine sleepiness or sedation levels. In some embodiments, the overall level of attention of the patient is assessed to help determine sleepiness or sedation levels.

The present invention is not limited to the aforementioned means of measuring sleepiness or sedation. For example, in some embodiments, the Stanford Sleepiness Scale (SSS), the psychomotor vigilance task (PVT), the Epworth Sleepiness Scale (ESS), the Chalder Fatigue Scale (CFM), the Fatigue Severity Scale (FSS), the Pasero Opioid-Induced Sedation Scale (FOSS), the like, or a combination thereof used to help assess sleepiness or sedation.

In some embodiments, the method comprises evaluating a biological sample (e.g., blood or other appropriate biological sample) of the individual. For example, in some embodiments, the method comprises assessing peripheral levels of the serotonin 2A receptor. In some embodiments, the method comprises assessing peripheral levels of the serotonin 1A receptor. The results of the biological sample evaluation may be correlated with a diagnosis of schizophrenia as appropriate.

In some embodiments, the method comprises subjecting the patient to a positron emission tomography (PET) scan, e.g., to evaluation levels of brain serotonin 2A receptor (5-HT2AR) and/or serotonin 1A receptor (5-HT1AR). In some embodiments, the method comprises subjecting the patient to an electroencephalogram (EEG) (e.g., waking and sleep, at baseline, following antipsychotic administration, etc.). Data from these tests may be used to help determine a diagnosis of schizophrenia.

The present invention also features a kit comprising the dose of the medication. In some embodiments, the kit further comprises a questionnaire. In some embodiments, the kit further comprises a set of instructions for evaluating the patient.

For reference, FIG. 1, FIG. 2A, FIG. 2B, FIG. 2C, FIG. 3A, FIG. 3B, FIG. 3C, FIG. 3D, FIG. 3E, FIG. 4A, FIG. 4B, FIG. 4C, FIG. 4D, FIG. 5A, FIG. 5B, FIG. 5C, FIG. 6A, FIG. 6B, FIG. 6C, and FIG. 6D together show data showing differences between Egr3 deficient mice (knock out (KO) mice) and wild type mice (WT), e.g., differences in EEG recordings between Egr3 KO mice compared to WT mice in response to clozapine administration (and show differences in epoch-by-epoch beta activity of the two types of mice). For example, FIG. 1 shows that there can be a marked difference in the pattern of response to clozapine in Egr3 KO mice. Without wishing to limit the present invention to any theory or mechanism, it is believed that there is a correlation between susceptibility to sedation in schizophrenic patients (or in animal models that may attempt to simulate schizophrenia or schizophrenia-like conditions). This may be used to help distinguish schizophrenia from other causes of psychosis, e.g., psychiatric illnesses (e.g., bipolar II disorder, major depression with psychotic features, delusional disorder, PTSD), medical illnesses (e.g., delirium, toxicity of a drug, imbalance of electrolytes, hormones, other metabolic disturbances, infection, etc.), effects of drugs or alcohol, etc.

Figure 5A:
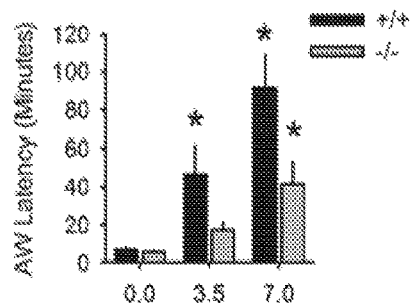
FIG. 5A shows latency to 2 minutes accumulated active wakefulness (AW) after vehicle or clozapine administration (in wild type mice +/+ and Egr3-deficient mice −/−).
Figure 5B:
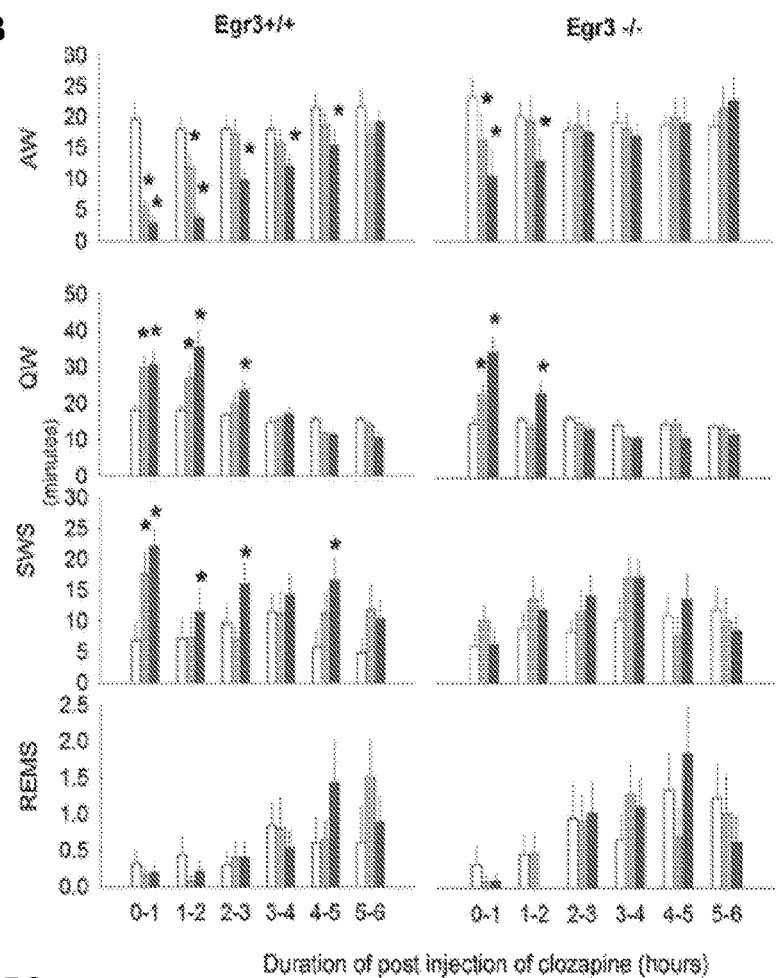
FIG. 5B shows time spent in wakefulness and sleep after vehicle or clozapine administration (in wild type mice +/+and Egr3-deficient mice −/−).
Figure 5C:
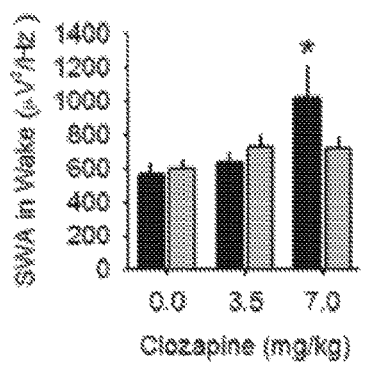
FIG. 5C shows slowing of the waking EEG (SWA; 1-4 Hz) during the 2 hr interval after clozapine administration. Data are shown as mean values +/− standard error of the mean. Asterisks indicate significant differences compared to vehicle treatment. Sex differences were not detected.

FIG. 3A, FIG. 3B, FIG. 3C, FIG. 3D, FIG. 3E, FIG. 4A, FIG. 4B, FIG. 4C, FIG. 4D, FIG. 5A, FIG. 5B, FIG. 5C, FIG. 6A, FIG. 6B, FIG. 6C, and FIG. 6D investigate sleep and waking behavioral phenotypes in Egr3-deficient mice associated with serotonin receptor 5-HT2 deficits. FIG. 3A-3E shows the effect of Egr3 disruption on the EEG power profiles of different wake and sleep states. FIG. 4A-4D show responses to sleep disruption. FIG. 5A-5C show clozapine-induced changes in waking and sleep in Egr3-deficient mice and wild type mice. FIG. 6A-6D show changes in waking after 5-HT2 antagonists treatment in Egr3-deficient mice.

In some embodiments, the evaluation for determining the level of sedation comprises using a Bispectral Index (derived from an EEG-related algorithm). For example, the Bispectral Index (BIS) is a scale of sedation from 0 to 100, wherein 100 is awake and 0 is a flatline EEG. In some embodiments, a high level of sedation is a BIS of 80 or less. In some embodiments, a high level of sedation is a BIS of 70 or less. In some embodiments, a high level of sedation is a BIS of 60 or less. In some embodiments, a high level of sedation is a BIS of 50 or less. In some embodiments, a low level of sedation (e.g., a level of sedation towards no sedation) is a BIS of 70 or more or 80 or more. In some embodiments, a low level of sedation is a BIS of 90 or more. Other sleepiness scales or methods for determining levels of sedation may be correlated with the BIS scale.

High levels and low levels of sedation are well known to one of ordinary skill in the art and recognized by presentation, e.g., a high level of sedation is that when a patient does not respond to verbal stimulus and/or physical stimulus or the patient is in a deep hypnotic state. A low level of sedation may be that when a patient is awake and can respond to verbal stimuli. The present invention is not limited to the aforementioned examples of sedation levels.

EXAMPLE 1

Example 1 describes an example of research used to help determine parameters for determining the level of sleepiness or sedation (or lack thereof) that is associated with schizophrenia or a lack of schizophrenia. EEG patterns in patients recently diagnosed with schizophrenia or schizophrenia-like disorders will be compared at baseline and after a typical dose of clozapine (or other antipsychotic medication). Subjects will undergo one to 5 hours of continuous videotaped EEG monitoring. Before and after drug administration, patients' somnolence will be rated using the Stanford Sleepiness Scale (SSS) and the Psychomotor Vigilance Task (PVT) (or other scale, e.g., ESS, CFM, FSS, POSS, etc.). Baseline and post-antipsychotic administration EEG and EMG recordings during both sleep and awake states will be read. Statistical analyses will be conducted to identify correlations between EEG response, scores on sedation assessments, and clinical diagnosis.

EXAMPLE 2

Example 2 describes an example of research used to help determine parameters for determining the level of sleepiness or sedation (or lack thereof) that is associated with schizophrenia or a lack of schizophrenia. EEG patterns in patients recently diagnosed with schizophrenia or schizophrenia-like disorders will be compared at baseline and after a typical dose of medication (e.g., ziprasidone, olanzapine, the like, combinations thereof, e.g., antipsychotics with receptor binding profiles designed to mimic the serotonin 2A receptor and dopamine D2 receptor binding profile of clozapine, etc.). Subjects will undergo 1 hour of continuous EEG monitoring (e.g., including continuous observation by at least one individual) before medication administration and 4 hours of continuous EEG monitoring (e.g., including continuous observation by at least one individual) after medication administration. Before and after drug administration, patients' somnolence or sedation may be rated using the a scale, e.g., the Stanford Sleepiness Scale (SSS), the Psychomotor Vigilance Task (PVT), the ESS, the CFM, the FSS, the POSS, the like, combinations thereof, etc. Baseline and post-medication recordings during both sleep and awake states will be read. Statistical analyses will be conducted to identify correlations between EEG response, scores on sedation assessments, and clinical diagnosis.

EXAMPLE 3

A 35-year-old male presents to the emergency department complaining of hallucinations. The attending physician requests a psychiatry consult. The psychiatrist orders a test according to the present invention: the patient is administered a dose of olanzapine at time zero; thirty minutes following the administration of the medication, the nurse evaluates the patient. The evaluation comprises the following tests: (a) respiratory rate measurement; (b) oxygen saturation measurement; and (c) pulse measurement. Since the patient appears relatively alert, the evaluation also comprises an eye test wherein the patient is asked to keep his eyes open for 10 seconds. The patient's respiratory rate, oxygen saturation, and pulse are not significantly altered by the administration of the medication. The patient has no difficulty keeping his eyes open for more than 10 seconds. Based on the results of the evaluation, the psychiatrist diagnoses the patient with a high probability of having schizophrenia. The psychiatrist makes medication decisions based upon the results of this test.

EXAMPLE 4

A 27-year-old female presents to the emergency department complaining of disorganized speech and abnormal motor behavior. The attending physician requests a psychiatry consult. The psychiatrist orders a test according to the present invention: the patient is administered a dose of olanzapine at time zero; thirty minutes following the administration of the medication, the nurse evaluates the patient. The evaluation comprises the following tests: (a) respiratory rate measurement; (b) oxygen saturation measurement; and (c) pulse measurement. Since the patient appears sedated, the evaluation also comprises a sternal rub and an eye test wherein the patient is asked to keep her eyes open for 10 seconds. Respiratory depression is observed, as is a decrease in pulse. The patient is barely aroused by a sternal rub. She is unable to keep her eyes open for more than 3 seconds. Based on the results of the evaluation, the psychiatrist diagnoses the patient with a high probability of not having schizophrenia.

EXAMPLE 5

Twenty patients enroll in a study to assess levels of sleepiness after taking certain antipsychotic drugs.

Two patients receive 20 mg ziprasidone, two patients receive 40 mg ziprasidone, and two patients receive 60 mg zipradisone. Two patients receive 2.5 mg olanzapine, two patients receive 5 mg olanzapine, two patients receive 7.5 mg olanzapine, and two patients receive 10 mg olanzapine. Six patients receive placebo.

The patients remain in the clinic for at least four hours while research assistants assess the level of sleepiness of the patients. A questionnaire is given every hour for four hours.

The disclosures of the following documents are incorporated in their entirety by reference herein: Williams et al., 2012, Neuropsychopharmacology 37: 2285-2298; Gallitano-Mendel et al., 2008, Neuropsychopharmacology 33: 1266-1275; McOmish et al, 2012, Neuropsychopharmacology 37: 2747-2755; Maple et al., 2015, ACS Chem Neurosci (7): 1137-42; Gronli et al., 2016, Sleep 39(12): 1-11.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for detecting a deficiency in serotonin 2A receptor activity, a deficiency in serotonin 2A receptor levels, elevations in serotonin 1A receptor activity, or elevations in serotonin 1A receptor levels in a patient displaying signs or symptoms of a psychotic disorder, said method comprising:

a. administering to the patient a dose of a second-generation antipsychotic medication, the patient being a human; and b. subjecting the patient to an evaluation at a time point following administration of the dose of the second-generation antipsychotic medication, the evaluation is for determining a level of sedation resulting from the dose of the second-generation antipsychotic medication, the level of sedation being in a range of high level of sedation to zero level of sedation;

wherein if the sedation is a high level of sedation with a score of 6, 7 or X according to Stanford Sleepiness Scale (SSS), a score of 15 or greater according to Chalder Fatigue Scale (CFM), or a score of 3 or 4 according to Pasero Opioid-Induced Sedation Scale (POSS), or a combination thereof, then the patient does not have a deficiency in serotonin 2A receptor activity or serotonin 2A receptor levels, or does not have an elevation in serotonin 1A receptor activity or serotonin 1A receptor levels, whereas if the sedation is a score of 1, 2, 3, or 4 according to Stanford Sleepiness Scale (SSS), a score of 0-12 according to Chalder Fatigue Scale (CFM), a score of 1 or 2 according to Pasero Opioid-Induced Sedation Scale (POSS), or a combination thereof, then the patient does have a deficiency in serotonin 2A receptor activity or serotonin 2A receptor levels, or an elevation in serotonin 1A receptor activity or serotonin receptor 1A levels; and c. administering an anti-schizophrenia medication to the patient if the patient has a deficiency in serotonin 2A receptor activity or serotonin 2A receptor levels, or an elevation in serotonin 1A receptor activity or serotonin receptor 1A levels.

2. The method of claim 1, wherein the second-generation antipsychotic medication comprises a selective 5-HT2AR antagonist, a 5-HT2AR inverse agonist, or a combination thereof.

3. The method of claim 1, wherein the time point following administration of the medication is from 5 to 10 minutes, from 10 to 30 minutes, from 15 to 60 minutes, from 5 to 120 minutes, from 10 to 180 minutes, or more than 180 minutes.

4. The method of claim 1, wherein a deficiency in serotonin 2A receptor activity is associated with schizophrenia or bipolar I disorder.

5. The method of claim 1, wherein the dose of the second-generation antipsychotic medication is effective for rendering a non-schizophrenic patient completely sedated with a score of X according to Stanford Sleepiness Scale (SSS), or a score of 4 according to Pasero Opioid-Induced Sedation Scale (FOSS), or a combination thereof, at the time point following administration of the second-generation antipsychotic medication.

6. The method of claim 1, wherein the evaluation comprises measurement of one or more of the following parameters: pulse, oxygen saturation, blood pressure, and respiratory rate.

7. The method of claim 1, wherein the evaluation comprises subjecting the patient to a stimulus and measuring the result of the stimulus.

8. The method of claim 7, wherein the stimulus comprises a sternal rub, nail bed pressure, or smelling salts.

9. The method of claim 1, wherein the evaluation comprises administering a questionnaire to the patient.

10. The method of claim 1, wherein the evaluation comprises determining whether the patient can keep his/her eyes open for a time period.

11. The method of claim 1, wherein the evaluation is an amount of time the patient spends in sleep during a period of time following administration of the second-generation antipsychotic medication.

12. The method of claim 1, wherein the second-generation antipsychotic medication is ziprasidone or olanzapine.

* * * * *